United States Patent [19]

Eberle

[11] Patent Number: 4,621,667
[45] Date of Patent: Nov. 11, 1986

[54] APPARATUS FOR THE EXTRACTING AND DEPOSITING OF MEASURED QUANTITIES OF LIQUIDS

[76] Inventor: Gunter Eberle, Gartenstr. 100, 7200 Tuttlingen, Fed. Rep. of Germany

[21] Appl. No.: 691,208

[22] Filed: Jan. 14, 1985

Related U.S. Application Data

[63] Continuation-in-part of Ser. No. 640,880, Dec. 15, 1975, abandoned.

[51] Int. Cl.[4] .............................................. B65B 3/12
[52] U.S. Cl. ..................................... 141/258; 141/27; 141/98; 141/283; 73/864.18; 74/526; 222/309; 422/100
[58] Field of Search ............... 222/309; 141/250–284, 141/27, 2, 18–26, 234–248, 98; 422/100; 73/864.13, 864.16, 864.17, 864.18; 74/526

[56] References Cited

U.S. PATENT DOCUMENTS 3,346,024 10/1967 Berman et al. ........................ 141/25
3,650,306 3/1972 Lancaster ............................ 141/238
4,335,760 6/1982 Kabadi et al. ....................... 141/258

FOREIGN PATENT DOCUMENTS 194878 3/1965 Sweden .
1011470 12/1965 United Kingdom .

Primary Examiner—Houston S. Bell, Jr.
Attorney, Agent, or Firm—Kevin B. Clarke

[57] ABSTRACT

A compact apparatus for the extraction and delivery of measured quantities of liquid characterized by a fine adjustment of the stroke of the operating rod whereby accurately controlled measured amounts of liquids may be lifted and delivered is disclosed.

6 Claims, 7 Drawing Figures

U.S. Patent  Nov. 11, 1986  Sheet 1 of 3  4,621,667

APPARATUS FOR THE EXTRACTING AND DEPOSITING OF MEASURED QUANTITIES OF LIQUIDS This application is a continuation-in-part of U.S. patent application Ser. No. 640,880, filed Dec. 15, 1975, now abandoned.

The invention relates to an apparatus for the extraction and delivery of measured quantities of liquid for medicinal use with vessels disposed in rows in a frame on a base plate and movable horizontally over which syringes are mounted in a row next to one another in bores in a liftable and lowerable holding plate, the piston rods or plungers of the syringes being operable together via a liftable and lowerable operating member such as a plate engaging an axially movable operating rod.

Such an apparatus is described in U.S. Pat. No. 3,498,342, in which the operating rod is hydraulically operated. A fine adjustment of the stroke of the operating rod, however, is not possible because the connecting hoses can expand or contract by a small amount. In addition the operating rod is inserted into the operating plate with a relatively large clearance. Furthermore, the hydraulic adjustment device takes up a relatively large amount of space.

An apparatus is claimed in an earlier German Patent Application P2407101.0.52 (German Specification No. 2407101), dated Apr. 8, 1976 provides a remedy in that an axial displacement of the operating rod via an operating lever may be carried out by hand. However, means for carrying out a stepless and free of clearance axial displacement of the operating rod are not described.

Other adjusting possibilities, for example, via a toothed rod with gears does not work satisfactorily because the catching projections used do not provide adjustment free of play.

With hydraulic or pneumatic adjusting devices leakage losses may also occur, after a period of time which is likewise disadvantageous.

The object of the invention is to provide an apparatus of the abovementioned type, which is compact and which provides a means by which the stroke of the operating rod can be accurately and finely adjusted.

In accordance with the present invention, there is mounted on the operating rod at least one carrying member which has an axial adjustment in a predetermined axial direction and which member is clamped to the operating rod.

More particularly, the invention provides an apparatus for controlling the extraction and delivery of measured quantities of liquids for diagnostic or medicinal purposes which comprises receiving vessels arranged in rows in a frame mounted on a base plate and movable horizontally, over which syringes are mounted in a row next to one another in bores in a liftable and lowerable holding plate the plungers of the syringes being operable together by an operating rod which is actuated by at least one liftable and/or lowerable member characterized in that the operating rod passes through bores in the member, a dosing lever pivoted on each liftable and/or lowerable member and formed with a cam surface to engage a further cam surface, movement of the lever tilting the member to drivingly engage the operating rod, subsequent pivoting of the lever and engagement of the cam surfaces causing axial movement of the operating rod.

Thus, if the carrying member is moved in an axial direction via a dosing lever the carrying member engages the operating rod free of play and moves the latter in an axial direction to operate the piston rods or plungers of the syringe. The liquid contained in the syringes is therefore delivered accurately. With a reversed direction of operation an accurately measured quantity of liquid can be drawn up by the piston rods or plungers of the syringes.

In its preferred embodiment, the present invention employs two such carrying members on the apparatus mounted on an axially movable operating rod with the carrying members operating in opposite directions. There are thus two dosing or operating levers one of which lowers the operating rod in the direction of the syringes and the other of which raises the operating rod in the opposite direction. The accuracy of the operation is thus further increased.

There are thus dosing levers one of which lower the operating rod and the other of which dosing levers raises the operating rod in the opposite direction. The accuracy of the operation is thus further increased.

When in operation one member is firmly connected to the operating rod and the other can freely slide thereon. Each member is formed with an eccentric bore through which an operating rod passes, the bore having two shoulders on the edges thereof displaced diammetrically opposite each other.

If either of the members is pivoted by its dosing lever the initial movement causes one of the eccentric bores to engage the operating rod and further pivoting of the lever moves the operating rod axially.

By a movement of the dosing levers in the opposite direction the operating rod is released.

In order to be able to adjust the stroke accurately, an adjustable stop may be provided in the path of movement of one member to limit the stroke of the operating rod.

It is preferred to have the stop formed as an adjusting screw. The adjusting screw is then screwed more or less deeply into the housing to adjust the stop. At the same time a very accurate indication of the adjustment of the stop is obtained.

It is preferred to mount spring contacts under the head of the adjusting screw which provides for locking the adjusting screw free of play.

On the dosing lever a projection may also be provided to engage a stop. With this embodiment the stroke of the operating rod is increased.

The invention will be described with reference to the accompanying drawings.

Figure 1:
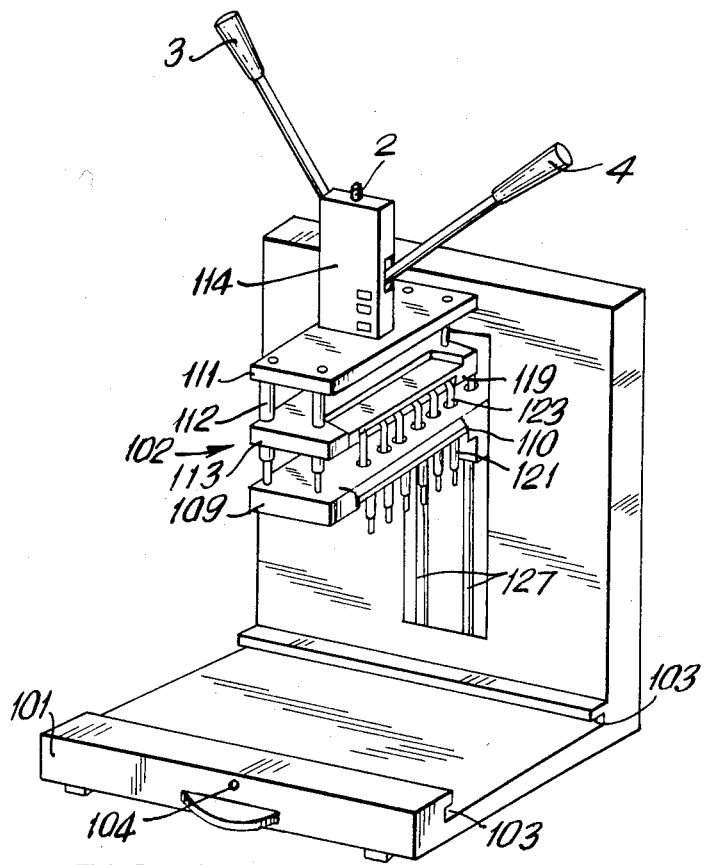
FIG. 1 is a perspective view of the apparatus.

The apparatus comprises a base plate 101 formed with guide ways 103 for sliding carriers (not shown) upon which are mounted frames for supporting dot plates and micro-plates of varying sizes or other test tubes used in the analysis or supply of medicinal liquids, the carriers being correctly located in the guideway 103 by springs 104 below a dosing unit 102 which is mounted in vertical guideways 127, the unit being lowered to register with the test tubes and raised therefrom.

After the carrier has been located in position below the unit 102 by hand the unit is lowered onto the test tubes.

The dosing unit 102 is formed as a frame comprising a plate 109 supported by a plate 110 engaging the guideway 127 syringes 121 being mounteds on a plate 111. A pressure plate 113 having an insert 119 to guide plungers of the syringes 121 is mounted for movement between the plates 109 and 111. The upper plate 111 and the plate 109 are rigidly connected to four vertical columns 112 arranged at the corners of the plates.

The columns 112 pass through holes in the pressure plate 113 which is thus movable between the plate 109 and upper plate 111 without tilting.

On the upper plate 111 there is arranged a feed unit 114 which is connected via an operating rod 2 through the upper plate 111 to the pressure plate 113 to control the movement in both directions. The feed unit is more precisely described with reference to FIGS. 2 to 6.

Figure 2:
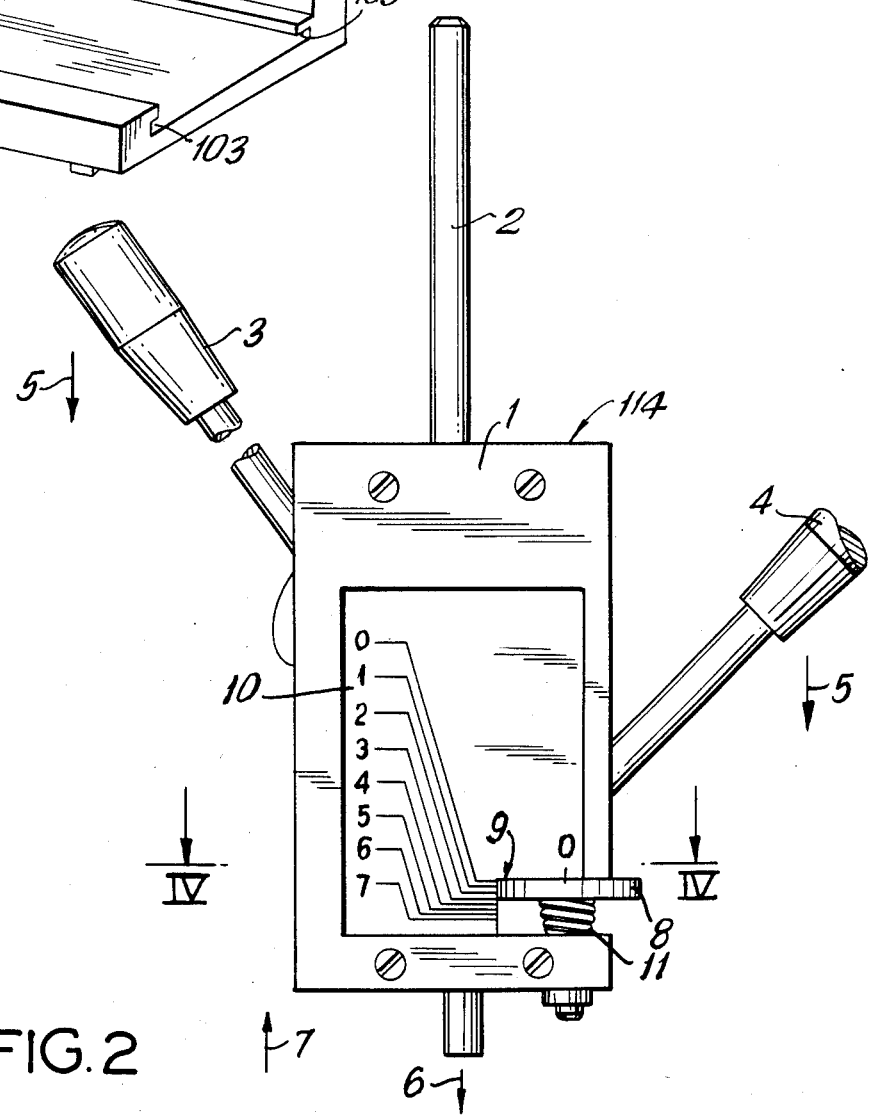
FIG. 2 is an elevation of the adjusting unit of the apparatus.

FIG. 2 shows a housing 1 of the feed unit 114 of FIG. 1. By a movement of the dosing lever 4 in the direction of the arrow 5 the operating rod 2 is moved in the direction of the arrow 6 i.e. downwards as hereinbefore described. By a movement of the dosing lever 3 in the direction of the arrow 5 the operating rod 2 is moved in the direction of the arrow 7, that is, upwards as hereinafter described. It is of advantage if each dosing lever is only moved in one direction, that is, if one of the dosing levers carries out the upward movement the other effects the downward movement of the operating rod 2.

By means of an adjusting screw 8 the stroke of the dosing lever 4 can be adjusted in the direction of the arrow 5. The upper edge of the adjusting screw 8 is so designed that is indicated on a dial (FIGS. 2 and 4) the adjustment of the stroke. For example, scale 10 on the housing 1 indicates that the adjusting screw 8 can be given a numerical movement from zero to seven etc. The stroke adjustment by the screw 8 is so accurate that a movement through a small angle alters the stroke of the dosing lever.

In order to exclude any play a counter spring 11 is provided which keeps the adjusting screw 8 in the respective position.

Figure 3:
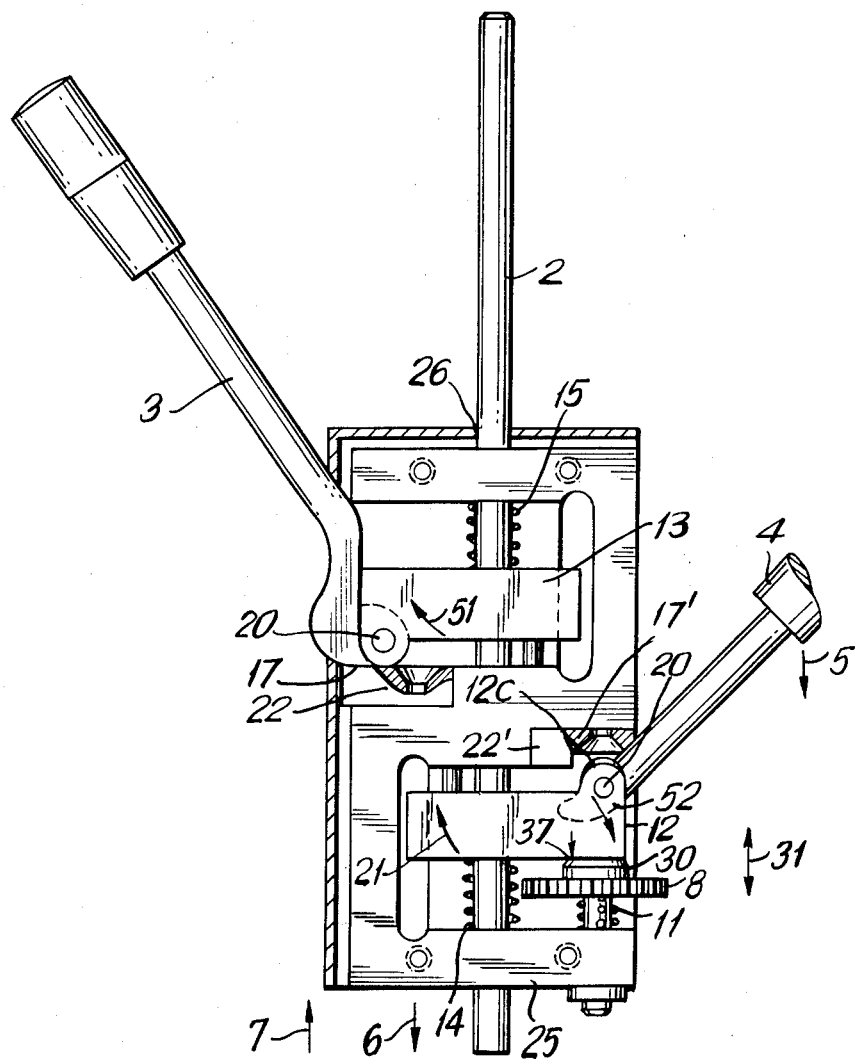
FIG. 3 is an elevation corresponding to FIG. 2 with the cover plate removed and partly in section.
Figure 4:
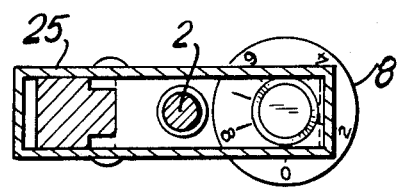
FIG. 4 is a section on line IV—IV of FIG. 2.

FIGS. 3 and 4 show further details. From these figures it can be seen that the operating rod 2 passes through a member 12 and is capable of moving the rod 2 in the direction of the arrow 6. In addition there is located above the member 12 a further, identical member 13 which is mounted as a mirror image of the member 12 i.e. it is inverted through a 180° and also engages the operating rod 2 and is capable of moving in the direction of the arrow 7. In order to avoid play a counter spring 14 engages the underside of the lower member 12 and a counter spring 125 engages the upper side of the upper member 13.

Figure 5:
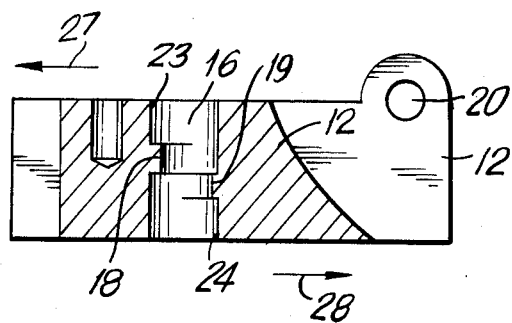
FIG. 5 is a vertical section through a carrying member which is used in the apparatus.
Figure 6:
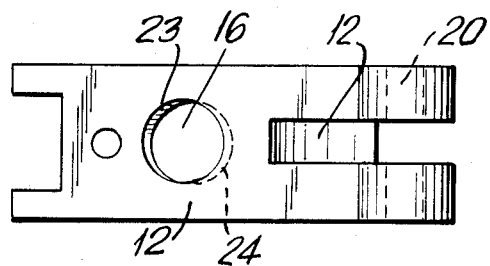
FIG. 6 is a plan of FIG. 5.

The members 12, 13 are each formed with holes 16 therethrough (see FIGS. 5 and 6). Each hole 16 is formed with arcuate steps 18, 19 the step 18 being diammetrically opposite and above the step 19.

The members 12, 13 are pivoted about separate pivots 20 to their dosing lever.

The actuation of the member 12 through the lever 4 is effected as follows:

With both levers, 3, 4 members 12 and 13 it is essential that upon actuation in one direction the member is clamped to the rod 2 which is thus taken along therewith and that upon movement in the opposite direction the clamping is released so that the rod 2 remains stationary.

The dosing lever is formed with a cam surface engageable with a fixed surface, movement of the lever in one direction pivoting the respective member causing it to engage the rod and further movement causing the member and the rod to move together in that direction. A reverse movement of the dosing lever 4 withdraws the steps 18, 19 from engagement with the rod 2 and the rod remains in the lowered position. The lever 4 is limited in its stroke in the direction of the arrow 5 by means of the adjustable step by engagement with the screw 8.

With the movement of the lever 4 in the direction of the arrow 5 as above stated the operating rod 2, moves downward through bearings in the frames 25, 26 in the direction of the arrow 5.

Each hole 16 is obtained by first making a cylindrical drilling. The lower part of the wall of this hole is then machined eccentrically to within a few tenths of a millimeter to form the space 24 shown at the right hand side of FIG. 5.

In addition the wall of the bore 16 on the left hand side of FIG. 5 is similarly machined eccentrically to within a few tenths of a millimeter to form the space 23 on the other side of the bore 16.

The displacement of the edge 23 is effected in the direction of the arrow 27 whilst the displacement of the edge 24 hereinbefore described takes place in the direction of the arrows 28 (FIG. 5). The bore 16 with the two edges is shown in FIG. 6.

The upper member 13 is formed identical to the lower member 12 and is mounted on the operating rod 2 but displaced by 180°.

FIG. 3 shows that the dosing levers 3 and 4 have cam surfaces which engage operating surfaces 17, 17' (shown as a fixing screw) on members 22, 22' fixed to the housing and thus effect a pivoting of the member 13 in the direction of the arrow 51 and of the member 12 in the direction of the arrow 52 and subsequent axial movement of the members so that the operating rod 2 is thus moved upwardly or downwardly in the direction of the arrows 6, 7 respectively.

There are several ways for the adjustment of the stroke of the dosing lever 4. The most important is shown in FIGS. 3 and 4. A stop 30 is adjusted by the adjusting screw 8 upwards or downwards in the direction of the arrow 31, thus the distance 37 between the upper side of the stop 30 and the lower face of the members 12 may be varied. The member 12 is set in contact with the stop 30 with the dial on the screw 8 at 0 when the delivery orifice is closed and is adjusted therefrom according to the dosage required.

Together with the described clamping action a very accurate stroke adjustment and dosing is achieved because with the slightest movement of the dosing lever the member 12 is tilted to a certain extent and pivoted in the direction of the arrow 21, thus bringing the two edges 23, 24 o the bore 16 into contact on the operating rod 2. No wear takes place because contact is always ensured.

Figure 7:
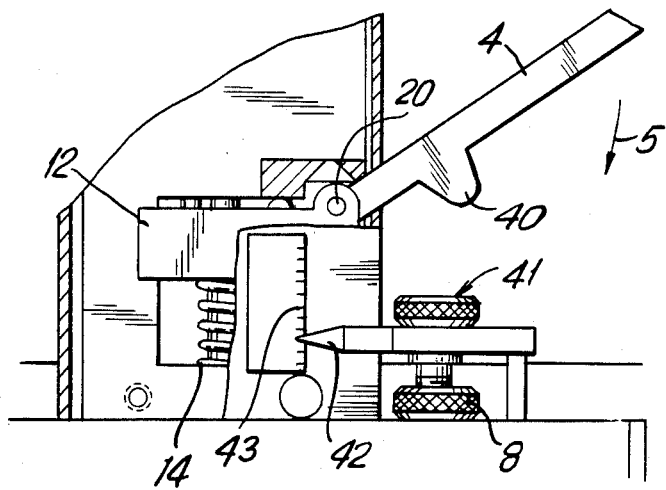
FIG. 7 is a view corresponding to FIG. 3 of a further embodiment.

A further arrangement for the limiting of the stroke is shown in FIG. 7 which operates as described with reference to FIG. 3 except for the substitution of stop 41. The dosing lever 4 has a projection 40 which comes into contact on the face of the stop 41 of the adjusting screw 8. With movement of the adjusting screw an indicator pin 42 is adjusted which indicates the adjusted stroke on a scale 43. With this arrangement longer strokes are provided than with the arrangement according to FIGS. 2 and 3.

What is claimed is:

1. Apparatus for the extraction and delivery of measured quantities of liquids into receiving vessels arranged in rows in a frame mounted in a horizontally movable base plate and over which syringes are arranged side by side in bores on a liftable and lowerable holding plate, piston rods in the syringes being operable together by means of an operating rod actuated by a liftable and lowerable member, characterized in that the operating rod passes through a bore in the liftable and lowerable member, a dosing lever is pivoted on the liftable and lowerable member and formed with a cam surface to engage a further cam surface, movement of the dosing lever tilting the liftable and lowerable member to drivingly engage the operating rod, subsequent pivoting of the dosing lever and engagement of the cam surfaces causing axial movement of the operating rod.

2. Apparatus as claimed in claim 1 wherein said bore in the liftable and lowerable member is an eccentric bore having two shoulders on the edges thereof displaced diametrically opposite each other for engagement of the operating rod when the liftable and lowerable member is pivoted by the dosing lever.

3. Apparatus as claimed in claim 1 wherein in the direction of the paths of movement of the liftable and lowerable member there is provided an adjustable stop which limits the stroke of the operating rod.

4. Apparatus as claimed in claim 3 wherein said adjustable stop is formed by an adjusting screw.

5. Apparatus as claimed in claim 4 wherein the adjusting screw is locked by means of spring contacts mounted under the adjusting screw.

6. Apparatus as claimed in claim 3 wherein there is provided on said dosing lever a projection which cooperates with said stop.

* * * * *